US008961179B2

(12) United States Patent
Longbottom et al.

(10) Patent No.: US 8,961,179 B2
(45) Date of Patent: Feb. 24, 2015

(54) APPARATUS AND METHOD FOR MINERALISING BIOLOGICAL MATERIALS

(75) Inventors: Christopher Longbottom, Dundee (GB); Joseph Crayston, Fife (GB); Nigel Berry Pitts, Dundee (GB); Dmitri Grinev, Dundee (GB); Iain Young, Dundee (GB)

(73) Assignees: The University of Dundee, Dundee (GB); The University of Abertay, Dundee, Dundee (GB); The University Court of the University of St. Andrews, Fife (GB)

( * ) Notice: Subject to any disclaimer, the term of this patent is extended or adjusted under 35 U.S.C. 154(b) by 814 days.

(21) Appl. No.: 12/668,687

(22) PCT Filed: Aug. 18, 2009

(86) PCT No.: PCT/GB2009/002008
§ 371 (c)(1),
(2), (4) Date: May 10, 2010

(87) PCT Pub. No.: WO2010/020769
PCT Pub. Date: Feb. 25, 2010

(65) Prior Publication Data
US 2012/0085647 A1   Apr. 12, 2012

(30) Foreign Application Priority Data
Aug. 18, 2008 (GB) .................................. 0815051.8

(51) Int. Cl.
*A61C 5/00* (2006.01)
*A61C 19/06* (2006.01)
(Continued)

(52) U.S. Cl.
CPC ............ *A61C 19/063* (2013.01); *A61B 5/0534* (2013.01); *A61B 5/4547* (2013.01); *A61N 1/306* (2013.01)
USPC .................................. 433/215; 604/20; 607/2

(58) Field of Classification Search
USPC .................... 433/215, 229; 604/20; 607/2, 51
See application file for complete search history.

(56) References Cited

U.S. PATENT DOCUMENTS 3,019,787 A * 2/1962 Simmons ..................... 604/20
4,060,600 A * 11/1977 Vit ................................ 424/53
(Continued)

FOREIGN PATENT DOCUMENTS

WO   WO 97/42909   11/1997
WO   WO 98/20869   5/1998
(Continued)

OTHER PUBLICATIONS

International Search Report for PCT International Application No. PCT/GB2009/002008 mailed Dec. 10, 2009.

*Primary Examiner* — Cris L Rodriguez
*Assistant Examiner* — Hao D Mai
(74) *Attorney, Agent, or Firm* — Foley & Lardner LLP

(57) ABSTRACT

An apparatus and method for mineralising demineralised and hypo-mineralised biological material such as tooth or bone. The apparatus has a probe electrode for receiving a mineralisation agent and a counter electrode. It is also provided with a controller to control the electrical signal provided to the probe such that the extent of mineralisation of the biological material is controlled by modulating or changing the electrical signal provided by the probe based upon the measured output of the circuit formed from the probe, counter electrode and biological material. The electrical output provides a measure of the extent of mineralisation of the biological material which is compared with data from a reference technique which gives 3D structural information on an area of interest in the biological material.

43 Claims, 6 Drawing Sheets

(51) Int. Cl.
*A61B 5/053* (2006.01)
*A61B 5/00* (2006.01)
*A61N 1/30* (2006.01)

(56) References Cited

U.S. PATENT DOCUMENTS

| | | | |
|---|---|---|---|
| 4,149,533 A | 4/1979 | Ishikawa et al. | |
| 4,266,533 A * | 5/1981 | Ryaby et al. | 600/14 |
| 4,456,012 A * | 6/1984 | Lattin | 607/3 |
| 5,267,997 A * | 12/1993 | Farin et al. | 606/38 |
| 5,425,641 A * | 6/1995 | Fischer | 433/226 |
| 6,191,190 B1 * | 2/2001 | Blackwell et al. | 523/115 |
| 6,997,883 B1 * | 2/2006 | Hahn | 600/560 |
| 2003/0208235 A1 * | 11/2003 | Miller et al. | 607/3 |
| 2006/0135407 A1 * | 6/2006 | Silcock et al. | 514/6 |
| 2007/0003905 A1 * | 1/2007 | Nguyen et al. | 433/215 |
| 2008/0097712 A1 * | 4/2008 | Bruce et al. | 702/77 |
| 2010/0303925 A1 * | 12/2010 | Pitts et al. | 424/602 |
| 2012/0252046 A1 * | 10/2012 | Fei et al. | 435/14 |

FOREIGN PATENT DOCUMENTS

| | | |
|---|---|---|
| WO | WO 2005/062710 A2 | 7/2005 |
| WO | WO 2008/101256 A2 | 8/2008 |

* cited by examiner

APPARATUS AND METHOD FOR MINERALISING BIOLOGICAL MATERIALS This application is a U.S. National Phase Application of PCT International Application No. PCT/GB2009/002008, filed Aug. 18, 2009.

FIELD OF THE INVENTION

The present invention relates to an apparatus and method for mineralising biological material and in particular for re-mineralising demineralised and hypo-mineralised tissue, such as tooth or bone.

BACKGROUND OF THE INVENTION

Caries is the decay of tooth or bone. Dental caries (also known as dental decay, caries or carious lesions) is caused by acids produced by microbial enzymatic action on ingested carbohydrate. The acids decalcify (demineralise) the inorganic portion of the tooth initially creating a sub-surface lesion, the organic portion then disintegrates leading to the creation of a cavity. In dentistry, demineralisation of a tooth through the development of a carious lesion can be described in terms of the depth of the carious lesion.

Dental caries is commonly treated by the removal of the decayed material in the tooth and the filling of the resultant hole (cavity) with a dental amalgam or other restorative material. In more severe cases, the entire tooth may be removed. Prior to lesion cavitation, it is possible to heal or reverse the tissue destruction by remineralising the caries lesions. However, this process works better where exogenous (e.g. salivary- or food-derived) proteins and lipids have been removed from the caries lesions.

It is known that the level of tooth decay alters the electrical characteristics of a tooth. This arises because as minerals are lost the porosity of the tooth increases and the consequent increased numbers of ions within the pores increase the conductivity i.e. the electrical transport in the tooth. Consequently, demineralisation of a tooth will result in an enhancement of its charge transport properties. This may be manifested in a decrease in the potential difference which must be applied to a demineralised tooth, compared with a healthy tooth, in order to achieve a comparable current therethrough. Correspondingly, this may be manifested in an increased current measurable from a demineralised tooth, compared with a healthy tooth, on application of the same potential difference. These effects can be detected on application of a constant current or constant potential difference respectively. Alternatively, the impedance (which includes the DC resistance) can be monitored by using AC signals.

There are a number of devices specifically designed to detect dental caries by the application of an alternating electrical current to a tooth using a probe or contact electrode and counter electrode. As described above, the main source of impedance in the circuit formed by the counter electrode and the probe is provided by the tooth and therefore, changes to the impedance of the circuit give a measure of changes in the impedance of the tooth. This technique is described in international patent application WO97/42909.

Iontophoresis is a non-invasive method of propelling a charged substance, normally a medication or a bioactive agent, using an electric current. It is known to use iontophoresis in transdermal drug delivery. Iontophoresis may also be used in conjunction with fluoride containing compounds to treat dentine hypersensitivity and to remineralise non-cavitated dental caries lesions. Iontophoresis devices typically include an active electrode assembly and a counter electrode assembly each coupled to opposite poles or terminals of a voltage source. The active agent can be cationic or anionic and the voltage source can be configured to apply the appropriate voltage polarity based upon the polarity of the active agent. The active agent may be stored in for example, a reservoir such as a cavity or in a porous structure or a gel.

SUMMARY OF THE INVENTION

It is an object of the present invention to provide an improved apparatus, system and method for mineralising biological material.

In accordance with a first aspect of the invention there is provided an apparatus for mineralising an area of interest in a biological material, the apparatus comprising:
a probe electrode for receiving a mineralisation agent;
a counter electrode;
a modulator adapted to produce an electrical input signal in a circuit formed from the probe electrode and the counter electrode and to cause the transfer of mineralising agent from the probe electrode to the biological material under the action of the electrical input signal;
a detector for detecting the electrical response of the circuit: and
a controller adapted to receive the detected electrical response of the circuit and to control the modulator so as to modify the waveform of the electrical input in response to the detected electrical response of the circuit.

Preferably, the modulator is adapted to modulate the shape of the waveform.

Preferably, the modulator is adapted to modulate the frequency of the waveform.

Preferably, the modulator is adapted to modulate the amplitude of the waveform.

Preferably, the modulator provides a single frequency or DC input.

Preferably, the detector measures the impedance and/or the DC resistance of the circuit.

Preferably, the modulator controls the current of the electrical input signal.

More preferably, the modulator provides a constant current.

Optionally, the modulator controls the voltage of the electrical input signal.

More preferably, the modulator provides a constant voltage.

Preferably, the apparatus further comprises a reference electrode adapted to control the electrical input signal.

Preferably, the reference electrode is located near the probe electrode.

Preferably, the probe electrode transfers the mineralising agent to the biological material by iontophoresis.

Preferably, the controller comprises a computer program.

Preferably, the controller comprises a first software module having a dataset which describes the characteristic electrical response of a sample biological material at various stages of mineralisation, and a second software module which compares said data with the detected electrical response to determine any modification required to the waveform of the electrical input.

Preferably, the dataset comprises the characteristic resistance or impedance response of said sample biological material.

Preferably, the dataset is derived from experimental data.

Preferably, the dataset provides 3D (3-dimensional) structural information on remineralisation. Preferably, the dataset provides quantification of the extent of remineralisation.

Preferably, the dataset in combination with the second software module provides 3D structural information on remineralisation of the biological material.

Preferably, the 3D structural information is provided in real time.

Preferably, the data in combination with the second software module provides quantification of the extent of remineralisation.

Preferably, quantification of the extent of remineralisation is determined in real time.

Preferably, the dataset comprises structural information which characterises mineral density in at least part of the area of interest.

Preferably, the second software module applies a function which defines the relationship between mineralisation and electrical response in order to compare said data with the detected electrical response and to determine any modification required to the waveform of the electrical input.

Alternatively, the second software module applies a look-up table containing information on the electrical response of teeth and their mineralisation in order to compare said data with the detected electrical response and to determine any modification required to the waveform of the electrical input.

Preferably, the probe electrode transfers the mineralising agent to the biological material by iontophoresis.

Preferably, the electrical response of the circuit indicates the presence of exogenous proteins and/or lipids in the area of interest.

Preferably, a conditioning agent is re-applied to the area of interest upon indication of the presence of said exogenous proteins and/or lipids.

Advantageously, the operation of the apparatus of the present invention can be interrupted in order to re-apply the conditioning agent thereby removing exogenous proteins and/or lipids.

In accordance with a second aspect of the invention there is provided a method of mineralising an area of interest in a biological material, the method comprising the steps of:

controlling the waveform of an electrical input signal in a circuit formed from the probe electrode and a counter electrode to transfer a mineralising agent to the biological material under the action of the electrical input signal;

detecting the electrical response of the circuit: and receiving the detected electrical response of the circuit and modifying the waveform of the electrical input in response to the detected electrical response of the circuit.

Preferably, the step of controlling the waveform comprises modulating the shape of the waveform.

Preferably, the step of controlling the waveform comprises modulating the frequency of the waveform.

Preferably, the step of controlling the waveform comprises modulating the amplitude of the waveform.

Preferably, the step of detecting the electrical response of the circuit comprises measuring the impedance and/or the DC resistance of the circuit.

Preferably, the current is modulated.

Optionally, the voltage is modulated.

Preferably, the electrical input signal is further controlled by a reference electrode.

Preferably, the reference electrode is located near the probe electrode.

Preferably, the step of receiving the detected electrical response of the circuit and modifying the waveform comprises comparing the dataset of characteristic electrical response of a sample biological material at various stages of mineralisation with the detected electrical response to determine any modification required to the waveform of the electrical input.

Preferably, the dataset comprises the characteristic resistance or impedance response of said sample biological material.

Preferably, the dataset is derived from experimental data.

Preferably, the dataset provides 3D structural information on remineralisation.

Preferably, dataset provides quantification of the extent of remineralisation.

Preferably, the dataset in combination with the software module provides 3D structural information on remineralisation of the biological material.

Preferably, the 3D structural information is provided in real time.

Preferably, the dataset in combination with the software module provides quantification of the extent of remineralisation.

Preferably, quantification of the extent of remineralisation is determined in real time.

Preferably, the dataset comprises structural information which characterises mineral density in at least part of the area of interest.

Preferably, the second software module applies a function which defines the relationship between mineralisation and electrical response in order to compare said data with the detected electrical response and to determine any modification required to the waveform of the electrical input.

Alternatively, the second software module applies a look-up table containing information on the electrical response of teeth and their mineralisation in order to compare said data with the detected electrical response and to determine any modification required to the waveform of the electrical input.

Preferably, the mineralising agent is transferred to the biological material by iontophoresis.

Preferably, the electrical response of the circuit indicates the presence of exogenous proteins and/or lipids in the area of interest.

Preferably, a conditioning agent is re-applied to the area of interest upon detection of the presence of said exogenous proteins and/or lipids.

Advantageously, the operation of the apparatus of the present invention can be interrupted in order to re-apply the conditioning agent thereby removing exogenous proteins and/or lipids.

In accordance with a third aspect of the invention there is provided a computer program comprising program instructions for implementing the steps of the method in accordance with the second aspect of the invention.

BRIEF DESCRIPTION OF THE DRAWINGS

The invention will now be described by way of example only with reference to the accompanying drawings in which:

FIG. 2a is a flow diagram which shows an embodiment of the method of the present invention and FIG. 2b is a block diagram of an apparatus for implementing the method of FIG. 2a;

DETAILED DESCRIPTION OF THE DRAWINGS

The present invention provides an apparatus and method for mineralising a biological material. The invention is particularly suitable for remineralisation of teeth where decay by demineralisation has occurred or for occluding dental tubules to treat dentine hypersensitivity, or for tooth whitening or in the treatment of dental erosion. It will be appreciated that the apparatus and method described herein is not restricted to the remineralisation of teeth but can be used to mineralise other biological material, for example, it may be used in the remineralisation of bones for the treatment of osteoporosis, osteopenia or periodontal disease.

In preferred embodiments of the present invention, spatial imaging data or 3D structural information can be used to generate different characterising parameters, including, tracking changes (and/or relative changes [bearing in mind that normally there is some variation in the mineral density of a healthy enamel and dentine]) in grey-scale values (in micro-CT images) in a variety of different parallel vectors in any one of many different planes, to generate an average representation of the mineral density changes in the direction of those vectors. The averaging process is performed preferably over the whole volume of the lesion; and the resulting information therefrom is processed to calculate, amongst other parameters, the depth of the carious lesion in the direction of the pulp. In view of the complex spatial geometries of lesions, the image analysis technique provides substantially more information than that normally available to a dentist. Thus, it may be possible to determine other lesion parameters which may be more useful in characterising the loss of mineral density than the traditionally-used lesion depth parameter.

As described previously, changes in the impedance and/or resistance of a tooth can be detected on the application of an AC signal or a DC constant current or constant potential difference. The application of a pulse or square-wave current or potential difference to a healthy or demineralised tooth also yields dynamic information from the plot of current (or potential) vs time.

Figure 1A:
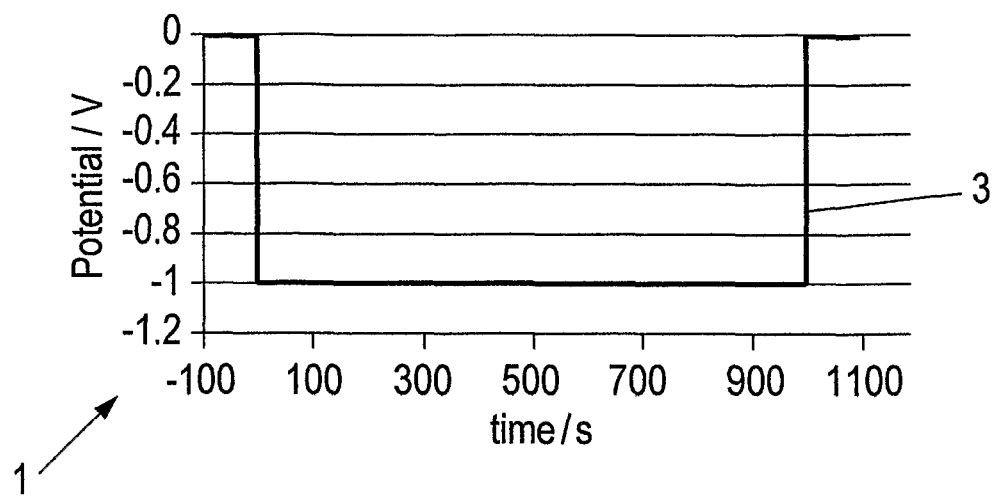
FIGS. 1a and 1b are graphs which show the applied voltage and the current decay rate for a healthy and a demineralised tooth.
Figure 1B:
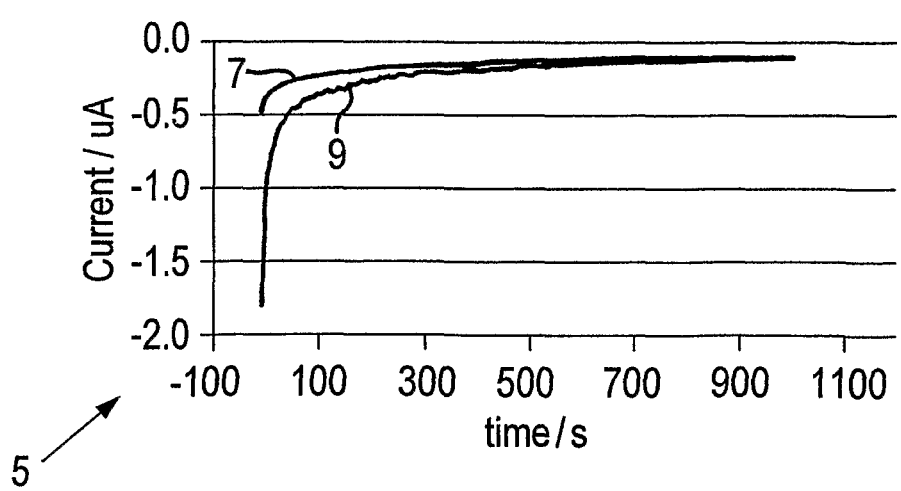

FIG. 1a is a graph 1 of voltage against time which shows a pulsed voltage 3 of substantially constant magnitude. FIG. 1b is a graph of current against time which shows the current decay rate in response to the applied potential difference (voltage) pulse for a healthy tooth and one which has been demineralised. The curve 7 shows the current response for the healthy tooth and the curve 9 shows the response for the demineralised tooth.

Using a mechanistic understanding of charge transport through a tooth and the effect of tooth demineralisation on tooth ionic conductivity, a relation may be formed between the mineral density profiles determined from the above-mentioned image processing technique and a measured temporal electrical response profile.

The present invention forms the relation through image-analysis and electrical properties analysis of a large number of healthy teeth and teeth with carious lesions by establishing an analytical model which creates a mathematical function to describe this relationship. Alternatively, the present invention may employ a look-up table between the measured electrical response data and average mineral density values (determined from the above image analysis techniques) obtained from the studies of the healthy and diseased teeth In establishing the above relation and/or look-up table, micro-CT techniques can be used in which data is calibrated against a plurality of phantoms, so as to ensure that the measured variation in grey scale values is actually representative of a change in mineral density though a tooth, as opposed to an aberrant effect (or imaging artifacts). The above process will be described in more detail below.

The apparatus of the present invention employs a feedback mechanism, wherein an electrical measurement (which may be AC or DC related) is made whilst a tooth is being remineralised by iontophoresis. The electrical measurement is related to the mineral density of a carious lesion in the tooth (through the above-mentioned relation and/or look-up table formed during an offline process) to calculate an appropriate control signal for the apparatus to optimally tune the iontophoretic process.

Figure 2A:
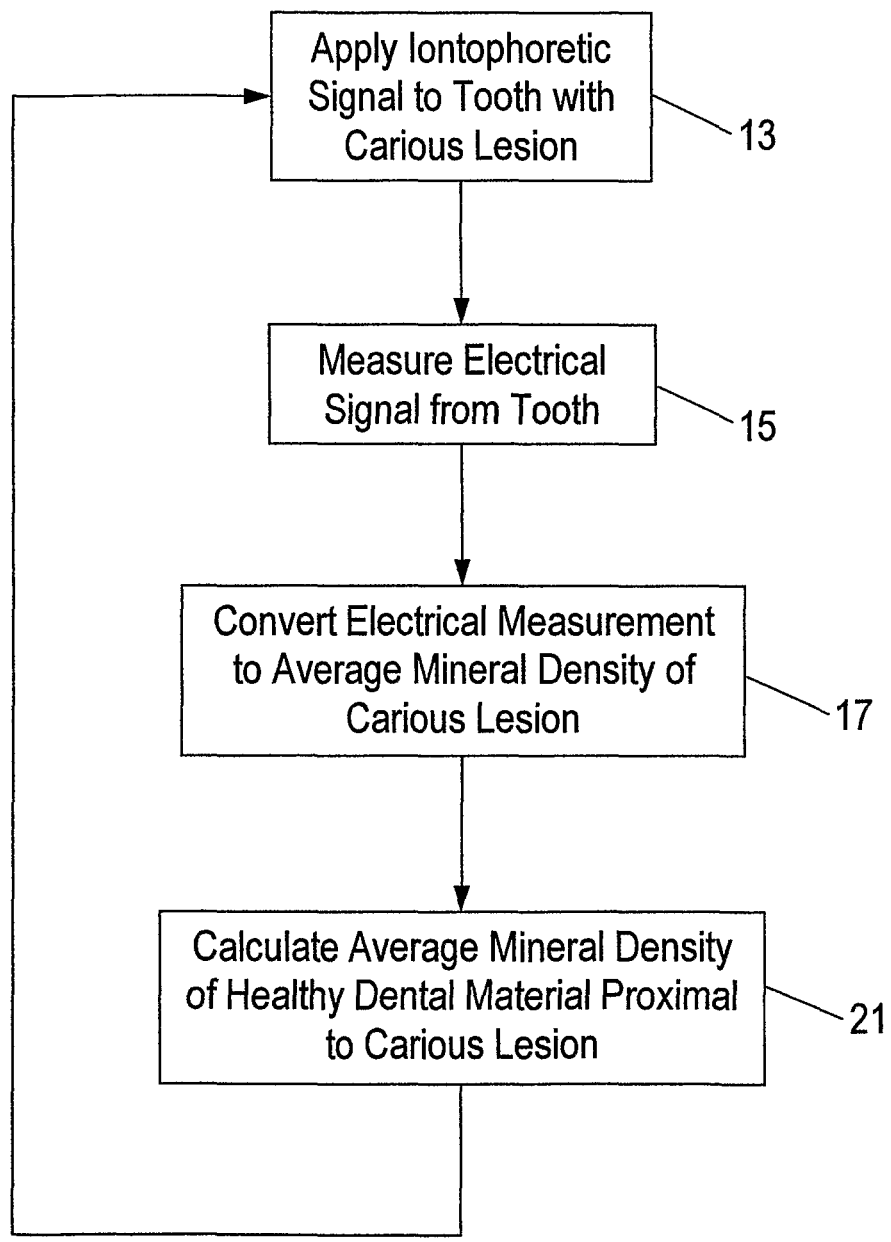

FIG. 2a shows an embodiment of the method of the present invention which comprises the following steps.

Step 0:

In first step towards calibrating the grey-scale values obtained from a micro-CT analysis (used in forming the mineral density values employed in the above-mentioned relation and/or look-up table) a plurality of phantoms (comprising a homogeneous isotropic material which substantially matches dental material) are scanned using a micro-CT device. In the present example, the phantoms comprise hydroxyapatite disks representing a particular material density.

Step 1:

Following the micro-CT analysis of the phantoms alone, a plurality of healthy teeth and teeth with carious lesions are each subjected to a similar scanning process, together with the phantoms. The calculated mineral densities of the scanned teeth are processed using a known segmentation technique to identify the boundaries of any lesions therein. A profile of the mineral density is established within the boundaries determined by the segmentation process; and the mineral density profiles are related to a steady-state or temporal electrical measurement obtained from the same teeth.

Step 2:

During iontophoresis, a constant potential difference or current is applied to a tooth with a carious lesion 13. An electrical response function is measured 15 from the tooth under treatment; and the relation (and/or look-up table) established in Step 1 is used to determine 17 the mineral density of the carious lesion.

Step 3:

The mineral density range of the healthy tooth material proximal to the boundaries established during step 1 is determined 19. This is used to establish the desired degree of remineralisation required of the iontophoretic treatment.

Step 4:

A change in the magnitude of iontophoretic signal is calculated 21, the calculated change being sufficient to drive mineral into the lesion so that the mineral density of the lesion more closely matches that of the healthy dental material.

Figure 2B:
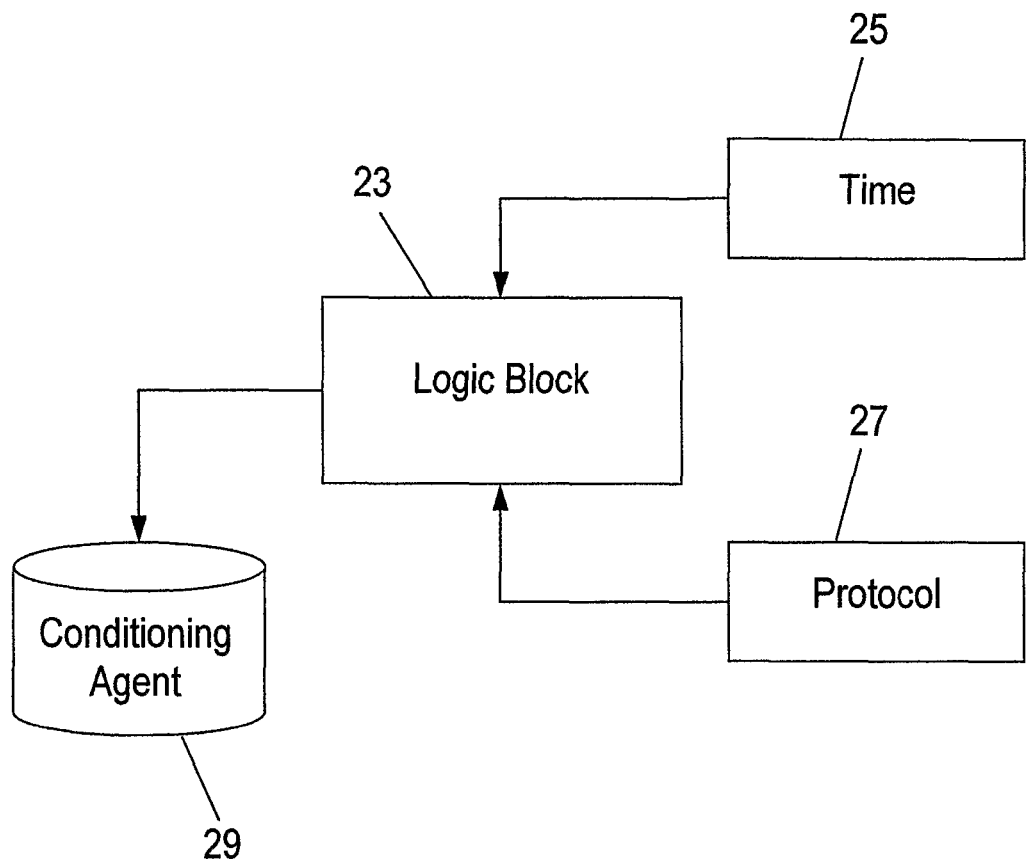

In implementing the method of FIG. 2a, the apparatus of FIG. 2b comprises a logic block 23, which in addition to receiving an indication of the desired change in the magnitude of the iontophoretic signal (from Step 4), receives information regarding the time 25 over which the iontophoresis treatment has been operating. The logic block 23 also receives additional protocol information 27 regarding times for example at which the iontophoresis should be started or stopped (e.g. to allow the electrical probe to be cleaned and further conditioning agent 29 to be applied thereto).

Figure 3:
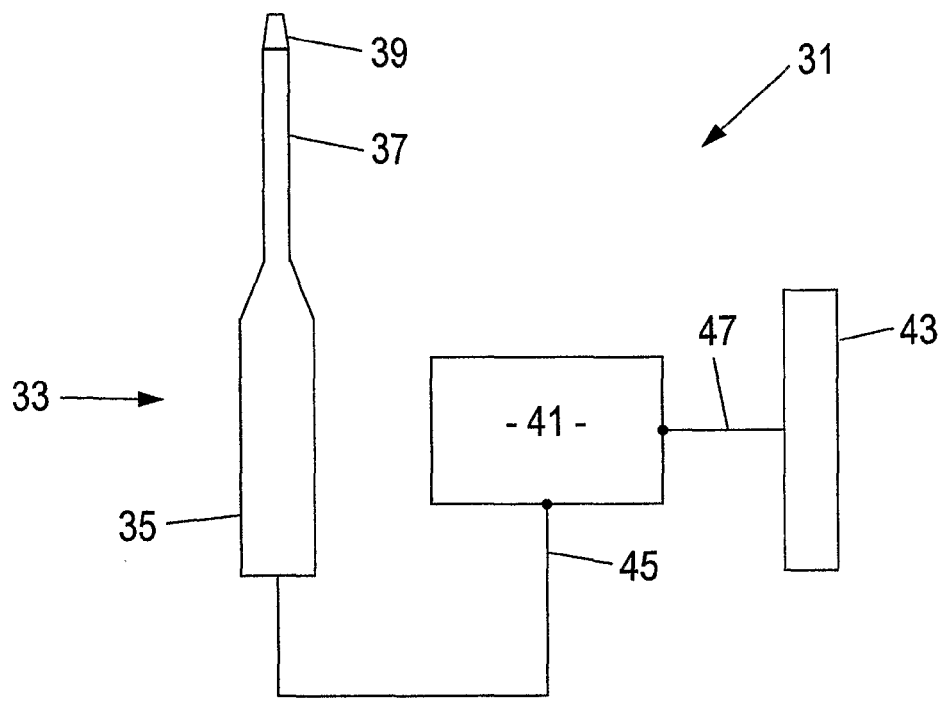
FIG. 3 is a schematic representation of a first embodiment of the present invention.

FIG. 3 shows another embodiment of an apparatus 31 for mineralising a biological material in accordance with the present invention comprising a probe 33 having a handle 35, a neck 37 and head 39. The probe 33 is connected to a controller 41 by cable 45 which in turn is connected to counter electrode 43 by cable 47. Electrode 43 may be a hand-held or mouth- or lip-"loop" electrode.

Figure 4:
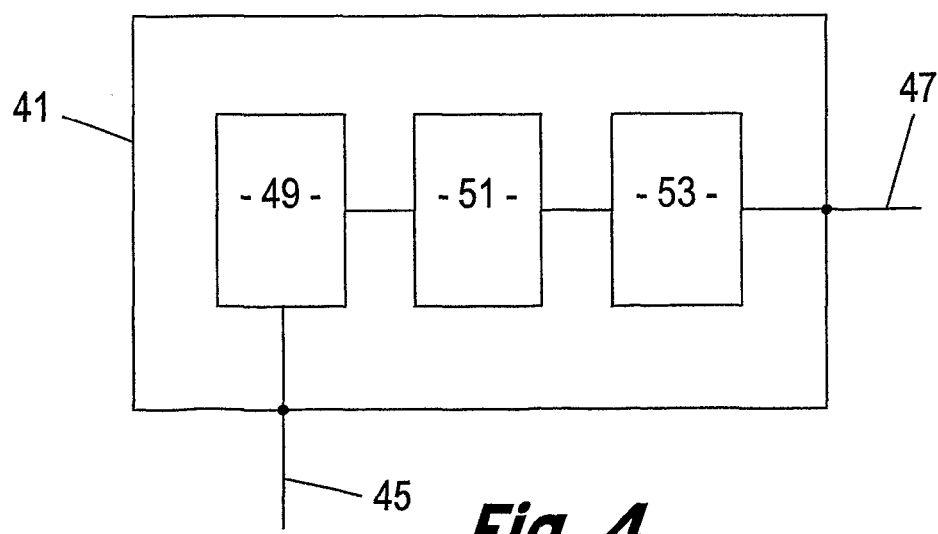
FIG. 4 is a more detailed schematic representation of the controller of the embodiment of FIG. 1.

FIG. 4 shows in more detail, the controller 41 which comprises a modulator 49 which modulates the shape and/or frequency and/or amplitude of the waveform sent to the probe 33.

Figure 5:
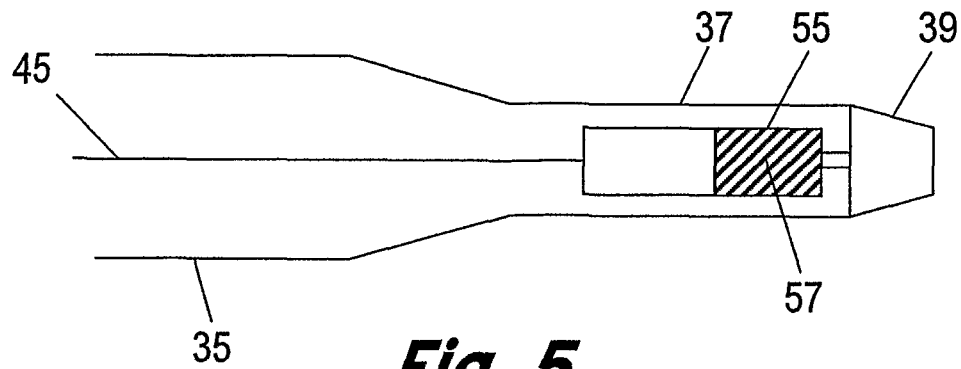
FIG. 5 is a more detailed schematic representation of the probe of the embodiment of FIG. 3.

FIG. 5 shows in more detail, the probe 33 of the apparatus of the first embodiment of present invention. In this embodiment, the cable 45 extends through the handle 35 of the probe 33 to a reservoir 55 containing a mineralising agent 57. The mineralisation agent is pushed out from the reservoir 55 through the head 39 of the probe 33 and in to contact with the biological material which in this example is a tooth.

In other examples of the present invention, the active agent may be stored in other ways such as in a porous structure or a gel which may be applied directly to a tooth. In embodiments of the present invention where the mineralising agent is stored in a chamber in the probe it can be introduced onto the probe surface by making the chamber of flexible material to allow the mineralising agent to be squeezed out. Alternatively, the chamber could have a plunger or similar component which pushes the mineralising agent out of the chamber.

In order to prevent cross-infection the remineralising agent is typically held separately from the device or embodied as a detachable 'probe tip' which attaches/clicks to the end of the device.

Figure 6:
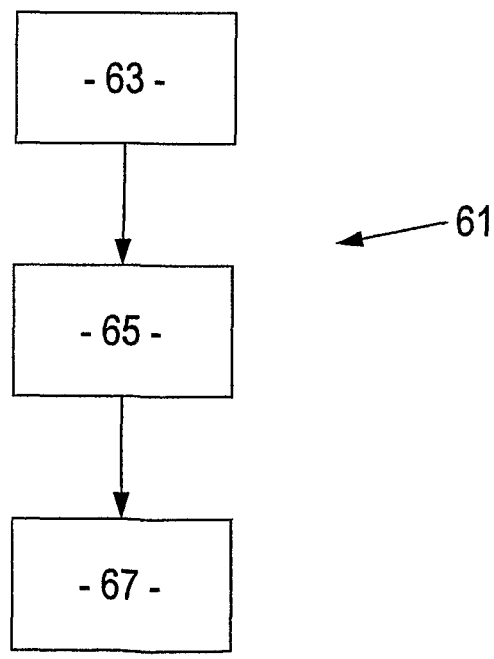
FIG. 6 is a flow diagram showing a first embodiment of the method of the present invention.

FIG. 6 is a flow chart 61 which shows a first embodiment of the method of the present invention. In the method of the present invention, the waveform of the electrical input signal in the circuit formed from the probe electrode and the counter electrode is controlled so as to transfer of a mineralising agent to the biological, material 63. The electrical response of the circuit is then detected 65 and the detected signal is analysed so as to determine whether and the extent to which the waveform of the electrical input should be modified in response to the detected electrical response of the circuit 67.

The following example of use of an embodiment of the present invention is given in relation to the remineralisation of teeth. The dentist identifies, within a patient, a specific tooth site which is to be remineralised. Thereafter a conditioning agent is applied and the site is cleansed to remove exogenous proteins and/or lipids from the site. The conditioning agent may be propelled into a hypo-mineralised or demineralised caries lesion, by iontophoresis, utilising the probe and counter electrodes, to optimise the disruption and removal of the exogenous protein and/or lipid content.

The probe 33 is inserted into the mouth of the patient and on to the tooth site. The counter electrode 43 is connected to the patient. The probe, which in this example comprises an iontophoretic device, propels the charged remineralisation agent 57 through the external surface of the tooth in order to remineralise the caries lesion at that tooth site.

During this process, the electrical circuit formed by the probe 33, patient and counter electrode 43 provides an output signal which identifies changes in the electrical response of the circuit which have been caused by the ongoing remineralisation process. The electrical response is detected by detector 53, the signal is passed to the controller 51 which processes and compares the electrical response to a dataset of known, experimentally obtained electrical responses to remineralisation. These responses provide 3D structural information on the amount and location of remineralisation of the tooth. The controller is therefore able to send program instructions to the modulator to alter the waveform of the electrical signal input to the probe 33 by changing its frequency and/or amplitude and/or shape. Once any change to the waveform has been determined, the modulator 49 provides an output to the probe 33 which in turn determines the manner in which the mineralising agent is propelled through the external surface of the tooth. A response to changes in the remineralisation pattern of the tooth can be made in real time or otherwise.

The comparison of the dataset of known, experimentally obtained electrical responses to remineralisation with the output signal detected by detector 53 requires the creation of a dataset or library of experimentally obtained responses. This information is derived from experimental data in which micro CT images are taken to provide virtual tooth slices. In this example of the present invention, the process is as follows.

A sample having dental caries, or other general defects (e.g. loss of mineral density), is scanned using a 3D tomography system (e.g. x-ray, MRI, neutron (ultrasound). A calibration phantom is used to determine the relationship between attenuation coefficient and electron density; hardware and software solutions are used to minimise intrinsic image artifacts (e.g. beam hardening, ring artifacts, scattering).

Reconstruction of the sample is achieved using acquired 2D angular projection images, and is accomplished for different voxel (i.e. 3D pixels) or spatial resolutions. 3D image processing algorithms are employed to calculate spatial distributions of electron density, as represented by attenuation data linked to the phantom. These distributions provide information on the degree of mineralization of relevant volumes of interest.

After iontophoretic remineralisation treatment, the sample is rescanned and subjected to the above mentioned methodologies. The subsequent distributions (before and after treatments) of mineral density of relevant volumes of interest are compared to inform of induced changes in mineralization patterns.

This process is repeated for samples with varying degrees of remineralisation to provide information on changes in internal sample structure, which can be related to changes in electrical responses of the sample which occurred during the treatment of the sample.

The described technique would inform any spatial heterogeneity of remineralisation, providing feedback from the electrical responses of the sample to the spatial location of remineralisation. Representative experimentally acquired datasets will be encoded into the device library to provide characteristic signatures of the spatial location and distribution of mineral densities which would enable the clinician to decide on real-time response to remineralisation patterns.

The feedback provided by the integration of the AC impedance or DC resistance values from the sample tooth and its incorporation in the controller, informs the settings of the device in order to optimise the remineralisation of the tissue. Suitably, the initial settings may involve the use of controlled potential coulometry where longer pulses are applied or chrono-amperometry where shorter pulses are applied. Feedback on the nature and extent of the remineralisation process provided by the present invention includes information about if and when to switch the settings to controlled current coulometry to optimise the remineralisation throughout the lesion.

In the case of controlled current coulometry the current is at a constant level which means that the flow of the remineralising agent would be constant also. This would be desirable in promoting a constant rate of remineralisation, since the rate of remineralisation is expected to be directly proportional to the amount of current flowing. Alternatively, the current may be allowed to fall as a function of time and so the rate of remineralisation is not constant with time.

Figure 7:
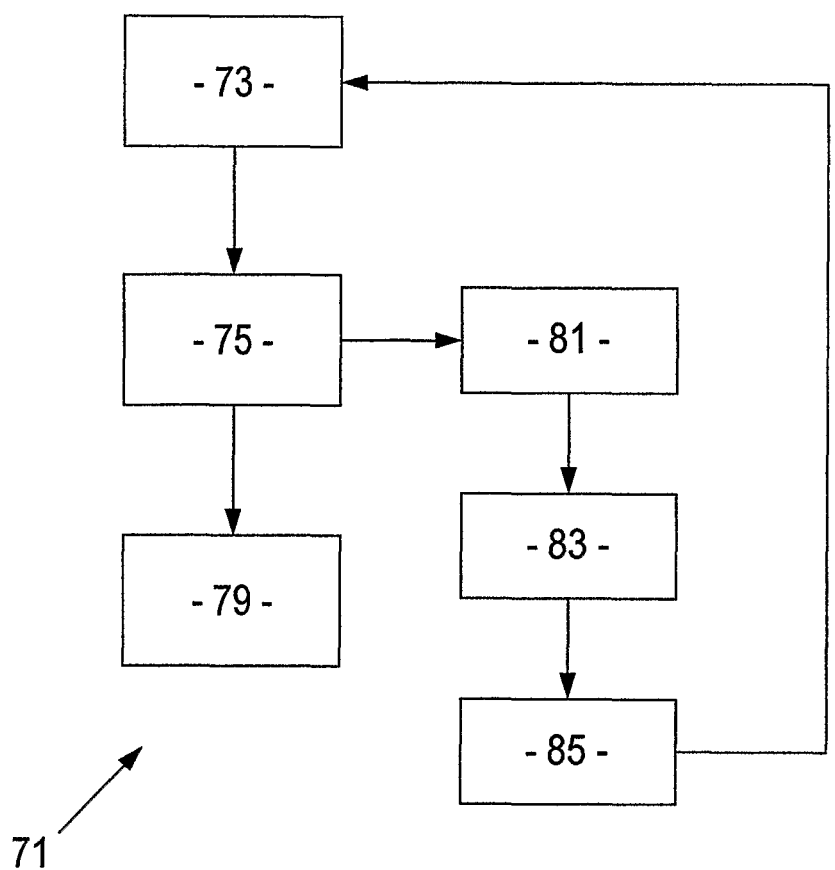
FIG. 7 is a flow diagram showing another embodiment of the method of the invention.

In the embodiment of the present invention shown in FIG. 7, in addition to characterising the state of mineralisation of the tooth, the electrical response of the circuit gives information indicative of the build-up of exogenous proteins and/or lipids in the area of interest. The flow diagram 71 illustrates the transfer of a mineralising agent to the biological material 73. The electrical response of the circuit is then detected 75 and the detected signal is analysed so as to determine whether and the extent to which the waveform of the electrical input should be modified in response to the detected electrical response of the circuit 77. In addition, the detector of the present invention is adapted to detect 81 changes in the electrical signal that are as a result of the build up of exogenous proteins, lipids and other materials. Once detected the remineralisation process is interrupted 83 and a conditioning agent is re-applied 85 for a specific period. Thereafter, the process of remineralisation may resume.

The presence of the exogenous proteins and/or lipids may be indicated by the apparatus of the present invention by analysis of the electrical response. In these circumstances, the user will be advised that a re-conditioning step is required and will take the appropriate action to re-apply a conditioning agent.

In another embodiment of the invention, the apparatus is provided with a reference electrode which in this example comprises a small Ag/AgCl wire placed close to the probe electrode. The reference electrode allows more precise control of electrical potential and is of particular use when large currents are required to treat large lesions.

The impedance of the tooth can be measured by the application of an AC signal as described above. Alternatively, a current interruption technique can be used whereby a current is applied for a certain amount of time and then the circuit is broken rapidly using a relay. The decay of the potential with time can give information on the resistance of the tooth.

In addition, the invention can be used in the preconditioning of, for example, a tooth where iontophoresis is used in preconditioning. A conditioning agent may be propelled into a hypo-mineralised or demineralised caries lesion, by iontophoresis to optimise the disruption of the exogenous protein and lipid content and then the polarity of the iontophoresis reversed, if required, in order to aid the removal of the proteinacious and other organic material from the hypo-mineralised or demineralised tissue. Examples of suitable agents include bleach, detergent, chaotropic agents such as urea, high phosphate concentrations, cocktails of proteases (e.g. endopeptidases, proteinases and exopeptidases) and any other protein solubilising, disrupting or hydrolysing agent. In this example of the present invention, the probe is attached to a detachable chamber containing a conditioning agent and iontophoresis is used with this chamber to propel the conditioning agent into the tooth prior to the remineralising step.

The apparatus and method of the present invention provides electrical feedback during iontophoretic conditioning to a detector and a controller which modifies the waveform of the electrical input in response to the detected electrical response of the circuit during conditioning.

Improvements and modifications may be incorporated herein without deviating from the scope of the invention.

The invention claimed is:

1. An apparatus for mineralising an area of interest in a biological material, the apparatus comprising:
a probe electrode for receiving a mineralisation agent;
a counter electrode;
a modulator adapted to produce an electrical input signal in a circuit formed from the probe electrode and the counter electrode and to cause a transfer of mineralisation agent from the probe electrode to the biological material under an action of the electrical input signal;
a detector for detecting a detected electrical response of the circuit; and
a controller adapted to receive the detected electrical response of the circuit and to control the modulator so as to modify a waveform of the electrical input signal in response to the detected electrical response of the circuit;
wherein: the controller comprises a first software module having a dataset which describes a characteristic electrical response of a sample biological material at various stages of mineralization, and a second software module which compares said characteristic electrical response with the detected electrical response to determine any modification required to the waveform of the electrical input signal.

2. The apparatus of claim 1 wherein the modulator is adapted to modulate a property of the waveform of the electrical input signal wherein the property is shape.

3. The apparatus of claim 1 wherein the modulator is adapted to modulate a property of the waveform of the electrical input signal wherein the property is frequency.

4. The apparatus of claim 1 wherein the modulator is adapted to modulate a property of the waveform of the electrical input signal wherein the property is amplitude.

5. The apparatus of claim 1 wherein the detector measures a property of the circuit, wherein the property is selected from the group consisting of impedance and DC resistance.

6. The apparatus of claim 1 wherein the modulator controls a property of the electrical input signal wherein the property is current.

7. The apparatus of claim 6 wherein the modulator provides a constant current.

8. The apparatus of claim 1 wherein the modulator controls a property of the electrical input signal wherein the property is voltage.

9. The apparatus of claim 8 wherein the modulator provides a constant voltage.

10. The apparatus of claim 1 wherein the apparatus further comprises a reference electrode adapted to control the electrical input signal.

11. The apparatus of claim 1 wherein the controller comprises a computer program.

12. The apparatus of claim 1 wherein the dataset comprises 3D structural information on mineralisation.

13. The apparatus of claim 1 wherein the dataset provides quantification of an extent of mineralisation.

14. The apparatus of claim 1 wherein the dataset in combination with the second software module provides 3D structural information on mineralisation of the biological material.

15. The apparatus of claim 12 wherein the 3D structural information is provided in real time.

16. The apparatus of claim 1 wherein the dataset comprises structural information which characterizes mineral density in at least part of the area of interest.

17. The apparatus of claim 1 wherein the second software module applies a function which defines a relationship between mineralisation and electrical response in order to compare said characteristic electrical response with the detected electrical response and to determine any modification required to the waveform of the electrical input signal.

18. The apparatus of claim 1 wherein the second software module applies a look-up table containing information on an electrical response of teeth and their mineralisation in order to compare said characteristic electrical response with the detected electrical response and to determine any modification required to the waveform of the electrical input signal.

19. The apparatus of claim 1 wherein, the probe electrode transfers the mineralisation agent to the biological material by iontophoresis.

20. The apparatus of claim 1 wherein the detector is adapted to indicate from the detected electrical response, a presence of exogenous proteins and/or lipids at the area of interest.

21. The apparatus of claim 20 wherein a conditioning agent is applied to the area of interest upon indication of the presence of said exogenous proteins and/or lipids.

22. A method of mineralising an area of interest in a biological material with an apparatus comprising:
a probe electrode for receiving a mineralisation agent;
a counter electrode;
a modulator adapted to produce an electrical input signal in a circuit formed from the probe electrode and the counter electrode and to cause a transfer of mineralisation agent from the probe electrode to the biological material under an action of the electrical input signal;
a detector for detecting a detected electrical response of the circuit; and
a controller adapted to receive the detected electrical response of the circuit and to control the modulator so as to modify a waveform of the electrical input signal in response to the detected electrical response of the circuit;
wherein: the controller comprises a first software module having a dataset which describes a characteristic electrical response of a sample biological material at various stages of mineralization, and a second software module which compares said characteristic electrical response with the detected electrical response to determine any modification required to the waveform of the electrical input signal;
the method comprising:
controlling the waveform of the electrical input signal in a circuit formed from the probe electrode and the counter electrode to transfer the mineralisation agent from the probe electrode to the biological material under the action of the electrical input signal;
detecting the detected electrical response of the circuit: and
receiving the detected electrical response of the circuit and modifying the waveform of the electrical input signal in response to the detected electrical response of the circuit.

23. The method of claim 22 wherein the controlling the waveform of the electrical input signal comprises modulating a property of the waveform of the electrical input signal, wherein the property is shape.

24. The method of claim 22 wherein the controlling the waveform of the electrical input signal comprises modulating a property of the waveform of the electrical input signal, wherein the property is frequency.

25. The method of claim 22 wherein the controlling the waveform comprises modulating a property of the waveform of the electrical input signal, wherein the property is amplitude.

26. The method of claim 22 wherein the step of detecting the electrical response of the circuit comprises measuring a property of the circuit, wherein the property is selected from the group consisting of impedance and DC resistance.

27. The method of claim 22 wherein a property of the electrical input signal is controlled and the property is current.

28. The method of claim 27 wherein the property of the electrical input signal is controlled to provide a constant current.

29. The method of claim 22 wherein a property of the electrical input signal is controlled and the property is voltage.

30. The method of claim 29 wherein the voltage is controlled to provide a constant voltage.

31. The method of claim 22 wherein the electrical input signal is further controlled by a reference electrode.

32. The method of claim 22 wherein the receiving the detected electrical response of the circuit and modifying the waveform of the electrical input signal comprises comparing the dataset with the detected electrical response to determine any modification required to the waveform of the electrical input signal.

33. The method of claim 32, wherein the dataset comprises a characteristic property of said sample biological material, said characteristic property being selected from the group consisting of impedance and DC resistance response.

34. The method of claim 32 wherein the dataset is derived from experimental data.

35. The method of claim 31 wherein the dataset provides 3D structural information on mineralisation of the biological material.

36. The method of claim 32, wherein the dataset provides quantification of an extent of mineralisation.

37. The method of claim 35 wherein the 3D structural information is provided in real time.

38. The method of claim 32 wherein the dataset comprises structural information which characterises mineral density in at least part of the area of interest.

39. The method of claim 32 wherein, the second software module applies a function which defines a relationship between mineralisation and electrical response in order to compare said characteristic electrical response with the detected electrical response and to determine any modification required to the waveform of the electrical input signal.

40. The method of claim 32 wherein the second software module applies a look-up table containing information on an electrical response of teeth and their mineralisation in order to compare said characteristic electrical response with the detected electrical response and to determine any modification required to the waveform of the electrical input signal.

41. The method of claim 22 wherein the mineralisation agent is transferred to the biological material by iontophoresis.

42. The method of claim 22 wherein the detected electrical response of the circuit indicates a presence of exogenous proteins and/or lipids at the area of interest.

43. The method of claim 42 wherein a conditioning agent is re-applied to the area of interest upon detection of the presence of said exogenous proteins and/or lipids.

* * * * *